US00PP10097P

United States Patent [19]

Stravers

[11] Patent Number: Plant 10,097

[45] Date of Patent: Nov. 4, 1997

[54] GERBERA PLANT NAMED 'TERANDARA'

[75] Inventor: Lambertus Johannes Maria Stravers, Kudelstaart, Netherlands

[73] Assignee: Terranigra Holding B.V., De Kwakel, Netherlands

[21] Appl. No.: 574,099

[22] Filed: Nov. 28, 1995

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,253 6/1990 Segers ..... Plt./68.1
P.P. 8,589 2/1994 Stravers ..... Plt./68.1

*Primary Examiner*—Howard J. Locker

[57] ABSTRACT

A new and distinct cultivar of Gerbera plant named 'Terandara', as illustrated and described, characterized by its semidouble type, distinct purple ray florets fading to a soft pink at the apex of the outer ray florets, very distinctive dark purple disc florets, the outermost florets which display white stigmas and the middle florets which show dark yellow anthers accentuated by anthocyanin stripes, and 70–85 mm overall flower diameter.

1 Drawing Sheet

BACKGROUND OF THE INVENTION

The present invention comprises a new and distinct cultivar of *Gerbera jamesonii*, referred to by the cultivar name 'Terandara'.

Terandara was originated from a hybridization program in De Kwakel, The Netherlands in 1991. The female parent was unnamed seedling M90.014 and the male parent was unnamed seedling M90.020. The female parent M90.014 is pink and single. It has a smaller flower diameter, a green center and longer stems compared to 'Terandara'. The male parent M90.020 has a different purple color and is less productive than 'Terandara'. Both have not been available outside Terra Nigra and are not patented in the United States. The new cultivar was selected by me from the progeny of the stated parentage on or about January 1992. The first asexual reproduction of 'Terandara' was accomplished when vegetative cuttings were taken on February 1992 in De Kwakel. The new cultivar is presently being propagated by cuttings and tissue culture. Horticultural examination of selected units initiated October 1992 has demonstrated that the combination of characteristics as herein disclosed for 'Terandara' are firmly fixed and are retained through successive generations of asexual reproduction.

'Terandara' has not been observed under all possible environmental conditions. The phenotype may vary significantly with variations in environment such as temperature, light intensity and day length. The following observations, measurements and comparisons describe plants grown in De Kwakel, The Netherlands, under greenhouse conditions which closely approximate those generally used in commercial practice.

The following traits have been repeatedly observed and are determined to be basic characteristics of 'Terandara', which in combination distinguish this Gerbera from its parents and all other varieties of which I am aware:

1. Type: Semi-double.
2. Color of ray floret: Purple.
3. Color of disc before flowering of disc florets: R.H.S. 187A.
4. Color of perianth lobe: Purple.
5. Diameter of flower head: 70–85 mm.

Of the many commercial cultivars known to me, there is no cultivar similar in comparison to 'Terandara'.

BRIEF DESCRIPTION OF THE FIGURE OF THE DRAWING

The accompanying photographic drawing shows typical inflorescence characteristics with the colors being as nearly true as possible in illustrations of this type. In the following description, color references are made to The Royal Horticultural Society Color Chart (R.H.S.). The color values were determined at 15:00 p.m. on 22 Sep. 1992 under natural light at De Kwakel.

BOTANICAL DESCRIPTION OF THE PLANT

Botanical: *Gerbera jamesonii* cv. Terandara.

Inflorescence

A. Capitulum:
*Form.*—Flat.
*Type.*—Semi-double.
*Diameter across face.*—70–85 mm.

B. Corolla of ray florets:
*Color (general tonality from a distance of 3 meters)*.—Purple.
*Color (topside)*.—R.H.S. 57A ending in R.H.S. 69B.
*Color (bottom side)*.—R.H.S. 61C.

C. Corolla of disc florets:
*Color (mature)*.—Purple.
*Color (immature)*.—R.H.S. 155B at base, at top R.H.S. 64A.

D. Reproductive organs:
*Stigma.*—White.
*Anthers.*—Dark yellow R.H.S. 22A.
*Pappus.*—R.H.S. 155B at base, at top R.H.S. 61A.

Plant

A. General appearance:
*Height.*—40 cm measured excluded any flowers.

B. Foliage:
*Color (abaxial)*.—R.H.S. 137B.
*Color (abaxial)*.—R.H.S. 147B.
*Shape.*—The angle of apex: acute. The shape of apex: pointed. The margin of lobes: crenate.

C. Disease resistance: No special disease resistance.

Other characteristics

The following traits have been repeatedly observed and are determined to be basic characteristics of 'Terandara', which in combination distinguish this Gerbera as a new and distinct cultivar.

Leaf blade:

*Length.*—Medium (approx. 45 cm).

*Width.*—Medium (approx. 18 cm).

*Thickness.*—Medium.

*Blistering.*—Weak.

*Pubescence.*—On upper side (midrib excluded): medium.

*Depth of cuts or incisions in leaf.*—Basal part: deep. Central part: deep. Distal part: shallow.

*Color.*—Upper side of the leaf blade: medium green (R.H.S. 137B). Bottom side of the leaf blade: R.H.S. 147B.

*Glossiness on upper side.*—Weak.

*Angle of apex.*—Acute.

*Shape of apex.*—Pointed.

*Margin of lobes.*—Crenate.

*Extensions of margin.*—Medium.

*Petiole length.*—Medium (approx. 12 cm).

*Petiole anthocyanin coloration.*—Medium.

Peduncle:

*Length.*—Medium (55 cm).

*Cross section.*—Elliptic.

*Tendency to fasciation.*—Medium.

*Thickness.*—Medium.

*Strength.*—Medium.

*Pubescence.*—Medium.

*Color.*—Medium green R.H.S. 145B.

*Anthocyanin coloration.*—At base: medium. At top: absent.

*Involucral bracts.*—Absent.

Flower head:

*Type.*—Semi-double.

*Diameter.*—Small (approx. 70–85 mm).

*Shape.*—Flat.

*Involucre.*—Height from point of attachment of involucre to top of flower head: medium (approx. 28 mm). Height: medium (approx. 20 mm). Diameter: medium (approx. 40 mm). Number of bracts: medium (approx. 39). Longitudinal axis of inner rows: reflexing. Anthocyanin: present. Pubescence: medium.

*Ray florets.*—Number: many (83). Shape: narrow elliptic. Longitudinal axis outer row: incurving/straight. Longitudinal axis inner row: straight. Longitudinal axis of ray female floret: straight. Longitudinal axis of ray male floret: reflexing.

*Outer ray floret.*—Cross section: flat. Length: short (approx. 30 mm). Width: narrow (approx. 8 mm). Longitudinal folding: weak. Angle of apex: acute. Shape of apex: pointed. Incisions of apex: one. Depth of incision: shallow. Color distribution on inner side: lighter to top. Edge of different color: present. Striation: absent. Claw spot: present.

Disc florets:

*Diameter.*—Small (approx. 14 mm).

*Main color perianth lobes.*—Female flowers: purple. Male flowers: purple.

Reproductive parts:

*Style.*—Main color distal part: pink R.H.S. 68B.

*Stigma.*—Main color: white.

*Anthers.*—Main color: dark yellow R.H.S. 22A. Color of top relative to other parts is darker. Longitudinal stripes are present. Intensity of anthocyanin coloration is medium.

*Pappus.*—Main color: yellow R.H.S. 1D. Color of top relative to other parts is identical. Level of top relative to closed disc florets: same level.

*Fertility.*—Fertility as well as the seed setting is medium.

I claim:

1. A new and distinct cultivar of Gerbera plant named 'Terandara', substantially as herein shown and described, characterized particularly as to novelty by the characteristics enumerated above.

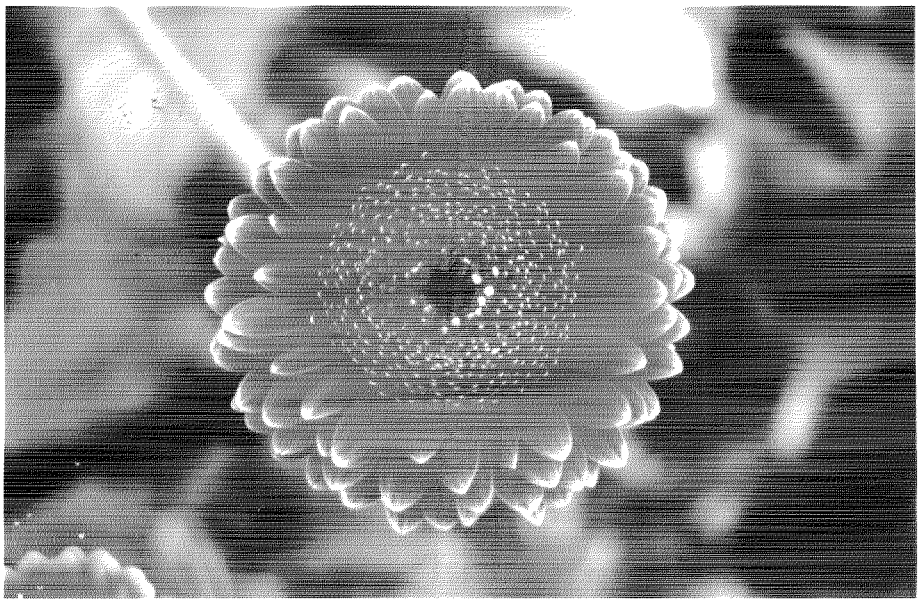

* * * * *